United States Patent [19]
Wolf

[11] 4,267,192
[45] May 12, 1981

[54] METHOD FOR TREATING INFLAMMATION
[75] Inventor: Milton Wolf, West Chester, Pa.
[73] Assignee: American Home Products Corporation, New York, N.Y.
[21] Appl. No.: 129,296
[22] Filed: Mar. 11, 1980
[51] Int. Cl.³ .................. A61U 31/19; A61U 31/235
[52] U.S. Cl. .................................... 424/308; 424/317
[58] Field of Search .............................. 424/308, 317
[56] References Cited
U.S. PATENT DOCUMENTS
3,780,061 12/1973 Allais et al. ................... 260/332.2 A
4,020,094 4/1977 Nelson ................................ 260/249

Primary Examiner—Stanley J. Friedman
Attorney, Agent, or Firm—George Tarnowski

[57] ABSTRACT

A method of treating inflammation in mammals by administering thereto compounds having the general formula:

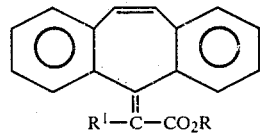

where R is hydrogen or alkyl of 1-4 carbon atoms, $R^1$ is hydrogen or an alkyl of 1-4 carbon atoms and pharmaceutically acceptable salts thereof.

4 Claims, No Drawings

METHOD FOR TREATING INFLAMMATION

This invention relates to a method of treating inflammation in mammals by the administration of dibenzocycloheptenylidenes.

In the treatment of chronic inflammatory conditions, both steroidal and nonsteroidal drugs have been extensively used. The use of corticosteroid therapy in rheumatoid arthritis for example, while providing symptomatic relief, has not been shown to actually improve prognosis and prolonged therapy is attended by serious side effects, such as increased susceptibility to infection, peptic ulceration and development of osteoporosis.

The non-steroidal anti-inflammatory agents, such as the salicylates, indomethacin, phenylbutazone, gold salts and the like, are also used in the treatment of chronic inflammatory diseases, especially rheumatoid arthritis. The non-steroidal drugs have a suppressive effect on the antigen-antibody reactions which are causative factors in the inflammatory process, and also have effects on the synthesis or release of prostaglandins, the complement system, lymphocyte transformations and so forth. However, as with the steroids, these anti-inflammatory agents, when used steadily to control chronic inflammatory conditions, have serious side-effects. The most serious is gastric intolerance, which severely limits the use of these agents in peptic ulcer patients. Moreover, phenylbutazone can cause bone marrow depression. Thus, the most widely used non-steroidal anti-inflammatory agents have some serious side-effects which limit their usefulness in the treatment of chronic inflammatory conditions.

The non-steroidal compounds used in the invention, however, are anti-inflammatory agents of considerable value in the treatment of inflammatory conditions, especially chronic conditions, with little or no secondary effects. The compounds are several times more potent than aspirin, but produce no gastric irritation, even at high doses.

The invention is directed to a method of treating inflammation in mammals by administering thereto an effective amount of a compound having the formula:

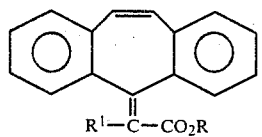

$R^1-C-CO_2R$ where R is hydrogen or an alkyl group of 1-4 carbon atoms, $R^1$ is hydrogen or an alkyl group of 1-4 carbon atoms, and pharmaceutically acceptable salts thereof.

The compounds of the invention can be prepared according to conventional general methods, for example by the Wittig-Horner reaction sequence described by C. D. Bergmann and A. Solomonovici, *Synthesis* 1970, pages 183–188. In the latter case, 5H-dibenzo-[a,d]cyclohepten-5-one is reacted with a trialkyl phosphonoalkanoate and sodium hydride in an organic solvent, the resulting alkyl 5H-dibenzo[a,d]cyclohepten-5-ylidene alkanoate is saponified with a base and then recovered as a salt or the free acid. The esters can be prepared either directly by the method just described or by esterifying the free acid. Moreover, the compounds can be prepared from 5H-dibenzo[a,d]cyclohepten-5-one via the Reformatsky reaction or via the modified Reformatsky reaction using lithium salts of α-lithiocarboxylic acids. The starting 5H-dibenzo[a,d]cyclohepten-5-one is a commercially available compound or it can be prepared according to W. Treibs and H. J. Klinkhammer, *Chem. Ber.*, 84, 671 (1951).

The pharmaceutically acceptable salts of the free acid include the sodium, potassium, ammonium, and lower alkylamine salts, which are prepared and isolated by conventional methods.

The compounds as used in the method of the invention are anti-inflammatory agents having significant oral activity in the treatment of inflammation. These compounds do not act by stimulating the steroids naturally occurring in mammals, nor do these compounds produce gastric secretion, even at high doses. Since these compounds additionally have a lack of general pharmacologic activity, they are of particular use in the long-term treatment of chronic inflammatory conditions, which, for example, are present in rheumatoid arthritis and other connective tissue disorders.

When the compounds of the invention are employed as anti-inflammatory agents, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth methyl cellulose, sodium carboxymethyl cellulose, low melting wax, cocoa butter, and the like. Diluents, flavoring agents, solubilizers, lubricants, suspending agents, binders, tablet-disintegrating agents and the like may be employed. The compound may be encapsulated with or without other carriers. In all cases the proportion of active ingredients in said compositions both solid and liquid will be at least sufficient to impart anti-inflammatory activity thereto on oral administration. The compounds may also be injected parenterally, in which case they are used in the form of a sterile solution containing other solutes, for example, enough saline or glucose to make the solution isotonic.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration level that will generally afford effective results without causing any harmful or deleterious side effects. With large animals (about 70 kg. body weight), for oral administration the dose is from about 10 milligrams to about 300 milligrams and preferably from about 10 milligrams to about 200 milligrams per day either as a single unit dose, or if desired, the dosage may be divided into convenient subunits administered at convenient times throughout the day.

The anti-inflammatory effects of the compounds of the invention may be demonstrated by standard pharmacological procedures, which are described more fully in the examples given hereinafter.

These procedures illustrate the ability of the compounds of the invention to exert an anti-inflammatory effect by directly measuring the effect of the compounds in the rat carrageenan edema test, the rat adjuvant arthritis test, and the in vitro prostaglandin synthetase activity assay, as well as the effects in the rat gastric irritation test.

EXAMPLE 1

(5H-Dibenzo[a,d]cyclohepten-5-ylidene)acetic acid

A mixture of 65.24 g. (0.291 moles) triethyl phosphonoacetate and 13.967 g. of 50% in oil (0.291 mole) sodium hydride in 750 ml. dry dimethyl sulfoxide is stirred overnight at ambient temperature in a nitrogen atmosphere. 60.00 g. (0.291 moles) 5H-dibenzo[a,d]cyclohepten-5-one is added to the mixture and after stirring at ambient temperature for one hour, the mixture is heated, with stirring, at 100°±1° C. for thirty hours. The dimethyl sulfoxide is distilled in vacuo and the oily residue refluxed with a solution of sodium hydroxide in 50% ethanol (400 ml. of 12.5%) for sixteen and one-half hours. The solvent is distilled in vacuo and the residue diluted with 100 ml. water. The mixture is extracted successively with 200 ml. of 1:1 toluene-heptane and 200 ml. toluene. The dark aqueous layer is decolorized with Darco G60 and then filtered through Celite. The clear dark solution of the sodium salt is added with stirring to 400 ml. 6 N hydrochloric acid. The title compound separates as a yellow solid. The yield of crude product is 67.7 g. (93.8%). Recrystallization of this material from tetrahydrofuran-toluene (with decolorization with Darco G60) gives a yield of 40.2 g. (55.7%) of off-white crystals having a melting point of 210° C. dec. (uncorr.).

Analysis for: $C_{17}H_{12}O_2$; Calculated: C, 82.24; H, 4.87; Found: C, 81.96; H, 4.91.

EXAMPLE 2

2-(5H-Dibenzo[a,d]cyclohepten-5-ylidene)propionic acid.

5H-Dibenzo[a,d]cyclohepten-5-one is reacted with triethyl 2-phosphonopropionate in a manner similar to Example 1, to yield the title compound, m.p. 235°-236° C. (uncorr.).

Analysis for: $C_{18}H_{14}O_2$; Calculated: C, 82.42; H, 5.38; Found: C, 82.33; H, 5.77.

EXAMPLE 3

Ethyl(5H-dibenzo[a,d]cyclohepten-5-ylidene acetate

A solution of triethyl phosphonoacetate (44.838 g., 0.200 mole) in dry dimethyl sulfoxide (100 ml.) is added rapidly with stirring to a solution of potassium-t-butoxide (23.005 g., 0.205 mole) in dry dimethyl sulfoxide (400 ml.) in a nitrogen atmosphere. The internal temperature rises from 23° C. to 33° C. After stirring for one-half hour at ambient temperature, 5H-dibenzo[a,d]cyclohepten-5-one (41.248 g., 0.200 mole) is added in a single portion. The resulting, deep wine-red solution is heated with stirring at 100°±1° C. for twenty-two hours. The solvent is distilled in vacuo and the residue diluted with water. The resulting mixture is extracted with methylene chloride (1×250 ml., 3×100 ml.) The combined extracts are successively washed with water (2×100 ml.), saturated salt solution (1×100 ml.), filtered through anhydrous sodium sulfate, then concentrated in vacuo to give an oil which solidifies on storage at room temperature. The yield of tan crystals melting at 61°-66° C. (uncorr.) is 50.4 g. (91.1%).

A portion (20.08 g.) of this material is recrystallized from hexane to give colorless crystals melting at 71.5°-72.5° C. (uncorr.) in a yield of 13.800 g. (69.0%). An additional crystallization from methylene chloride-pentane affords colorless prisms melting at 72.5°-73.5° C. (uncorr.).

Analysis for: $C_{19}H_{16}O_2$; Calculated: C, 82.58; H, 5.84; O, 11.58; Found: C, 82.54; H, 5.85.

EXAMPLE 4

Methyl(5H-dibenzo[a,d]cyclohepten-5-ylidene)acetate

Oxalyl chloride (2.665 g., 1.79 ml., 0.021 mole) is added to a suspension of (5H-dibenzo[a,d]cyclohepten-5-ylidene)acetic acid (5.000 g., 0.020 mole) in dry benzene (70 ml.). An exothermic reaction occurs and the solid gradually dissolves. After solution is complete, the mixture is refluxed for one hour, then concentrated in vacuo to give an amber oil which crystallizes on storage at ambient temperature. The yield of crude ester melting at 83.5°-84.5° C. (uncorr.) is 5.210 g. (99.31%). Recrystallization of the material from methanol affords colorless rods melting at 86.0°-86.5° C. (uncorr.) in a yield of 3.508 g. (66.86%).

Analysis for: $C_{18}H_{14}O_2$; Calculated: C, 82.42; H, 5.38; O, 12.20; Found: C, 82.43; H, 5.37.

Using this general procedure, other esters (e.g.) n-propyl, isobutyl etc. may be prepared.

EXAMPLE 5

The anti-inflammatory activity of a compound is assessed by its ability to inhibit experimentally induced edema in the hind paw of the rat.

Groups of 6-8 male Sprague-Dawley rats weighing between 150-200 grams are used. (5H-dibenzo[a,d]cyclohepten-5-ylidene)acetic acid (DCHA), ethyl(5H-dibenzo[a,d]cyclohepten-5-ylidene)acetate (EDCHA), methyl(5H-dibenzo[a,d]cyclohepten-5-ylidene)acetate (MDCHA), aspirin and indomethacin are administered orally in 0.5% methylcellulose. Vehicle alone is administered as a control. Sixty minutes after drug administration edema is induced by an injection of 0.1 ml. of a 1% carrageenan solution is saline into the subplantar tissue of the rat's right hind paw. Two minutes later, paw volume is measured volumetrically with a plethysmograph and again 3 hours later. The mean volume of swelling for the control group is calculated and compared to the test groups. Percent change in paw edema is calculated and analyzed statistically (unpaired, Student's t-test).

The results are summarized in Table 1.

TABLE 1

| | Treatment | Oral Dose mg/kg | Change in paw volume (ml) from 0-3 hr[a] | % Change |
|---|---|---|---|---|
| a | Control | — | 0.77 ± 0.05 | — |
| | DCHA | 3 | 0.63 ± 0.10 | −18 |
| | | 10 | 0.61 ± 0.05 | −21* |
| | | 30 | 0.48 ± 0.06 | −38** |
| | | 100 | 0.44 ± 0.07 | −43** |
| b | Control | — | 1.02 ± 0.10 | — |
| | DCHA | 10 | 0.53 ± 0.10 | −48** |
| | | 30 | 0.58 ± 0.08 | −43** |
| | | 90 | 0.44 ± 0.03 | −57*** |
| | Indomethacin | 1 | 0.65 ± 0.06 | −36** |
| | | 3 | 0.50 ± 0.07 | −51** |
| | | 9 | 0.32 ± 0.02 | −69** |
| c | Control | — | 1.00 ± 0.12 | — |
| | DCHA | 20 | 0.84 ± 0.10 | −16 |
| | | 60 | 0.47 ± 0.08 | −53** |
| | | 180 | 0.49 ± 0.06 | −51** |
| d | Control | — | 0.88 ± 0.10 | — |
| | Aspirin | 30 | 0.63 ± 0.02 | −28* |
| | | 90 | 0.54 ± 0.04 | −39** |
| | | 270 | 0.29 ± 0.10 | −67** |
| e | Control | — | 1.15 ± 0.05 | — |

TABLE 1-continued

| Treatment | Oral Dose mg/kg | Change in paw volume (ml) from 0-3 hr[a] | % Change |
|---|---|---|---|
| DCHA | 20 | 1.08 ± 0.05 | −6 |
|  | 60 | 0.82 ± 0.13 | −29** |
|  | 180 | 0.62 ± 0.04 | −46** |
| EDCHA | 20 | 1.11 ± 0.08 | −4 |
|  | 60 | 0.98 ± 0.06 | −15 |
|  | 180 | 0.87 ± 0.04 | −25** |
| Indomethacin | 5 | 0.54 ± 0.08 | −53* |
| Control | — | 0.74 ± 0.08 | — |
| MDCHA | 60 | 0.68 ± 0.08 | −8 |
|  | 120 | 0.59 ± 0.08 | −20 |
|  | 240 | 0.68 ± 0.10 | −8 |
|  | 480 | 0.59 ± 0.07 | −20 |

[a]Each value represents the mean ± S.E. of 6-8 animals
*p ≦ 0.05
**p ≦ 0.01
***p ≦ 0.001

The results show that (5H-dibenzo[a,d]cyclohepten-5-ylidene)acetic acid (DCHA) and its ethyl ester (EDCHA) inhibit carrageenan paw edema at oral doses of 10–180 mg/kg. The estimated $ED_{50}$ for DCHA is 80 mg/kg., while the estimated $ED_{50}$ for indomethacin and aspirin are 2.7 and 110 mg/kg., respectively.

EXAMPLE 6

A procedure similar to that of Example 5 is repeated except the rats are bilaterally adrenalectomized on day 0 and immediately placed on saline (0.9%) instead of water. The test is then done 7 days later as described in Example 5. Normal rats received the same doses as adrenalectomized rats. Compounds active in the normal animal but not adrenalectomized animals, are assumed to work thru the pituitary adrenal axis. Clinically effective anti-inflammatory drugs are independent of the adrenals for activity.

The results are summarized in Table 2.

TABLE 2

| Treatment | Oral dose mg/kg | Normal Rats Mean Edema (ml) ± S.E. | % Inhibition | Adrenalectomized Rats Edema (ml) ± S.E. | % Inhibition |
|---|---|---|---|---|---|
| Control | — | 0.94 ± 1.0 | — | 0.96 ± .15 | — |
| Control Sham |  |  |  | 1.00 ± .09 |  |
| DCHA | 100 | 0.58 ± .04 | 38* | 0.57 ± .02 | 37* |
| DCHA | 200 | 0.53 ± .05 | 44* | 0.81 ± .04 | 41* |
| Aspirin | 300 | 0.52 ± .07 | 44* | 0.64 ± .04 | 34[a] |
| Indomethacin | 5 | 0.42 ± .09 (0.97 ± 0.05) | 60* | 0.42 ± .09 (1.02 ± 0.1) | 59* |

[a]1/6 animals died
*p ≦ 0.05

The results show that in adrenalectomized rats, the anti-inflammatory activity of DCHA at 100 and 200 mg/kg. (orally) was not different from that observed in normal control animals in the same manner as aspirin and indomethacin. Thus, the activity of DCHA is independent of the adrenal glands.

EXAMPLE 7

Adjuvant Arthritis Test

A. Daily Administration

Polyarthritis is induced in groups of 6–10 Sprague-Dawley rats weighing between 180–220 g. by a subcutaneous injection into the right paw of dessicated *Mycobacterium butyricum* or *tuberculosis* (0.5 mg/0.1 ml.) suspended in light mineral oil. DCHA, indomethacin and phenylbutazone are administered orally in 0.5% methylcellulose using a daily regimen (except for weekends). Both hind paw volumes (ml.) are measured by mercury plethysmograph on day 0 or at the time of injection of the complete adjuvant. Increases in paw volume (viz. edema) are determined for both paws on days 4 and 16. The change in body weight from day 0 to day 16 is also calculated. Statistical analysis of differences in paw edemas and body weight is performed by using the unpaired. Student's t-test.

The results are summarized in Table 3.

TABLE 3

| | Treatment | Oral Dose mg/kg | Change In Body Weight (mean ± S.E.) 0–16 days | Increase in Right Paw Volume (ml.) (mean ± S.E.) 0–4 days | % Change of Right Paw Edema at Day 4 | Increase in Left Paw Volume (ml.) (mean ± S.E.) 0–16 days | % Change of Left Paw Edema at Day 16 |
|---|---|---|---|---|---|---|---|
| a | Control | — | 7.5 ± 8.6 | 1.56 ± .08 | — | 0.78 ± .10 | — |
|  | DCHA | 3.0 | 22.5 ± 9.6 | 1.33 ± .11 | −15 | 0.43 ± .09 | −45* |
|  |  | 10.0 | 25.6 ± 8.0 | 0.70 ± .06 | −55*** | 0.41 ± .04 | −47** |
|  |  | 30.0 | 45.8 ± 5.6** | 0.66 ± .06 | −58*** | 0.30 ± .05 | −62*** |
|  |  | 100.0 | 50.6 ± 5.4*** | 0.74 ± .08 | −53*** | 0.31 ± .05 | −60*** |
|  |  | 300.0 | 58.2 ± 8.3::: | 0.66 ± .05 | −58*** | 0.14 ± .06 | −82*** |
|  | Indomethacin | 0.1 | 16.9 ± 9.0 | 1.07 ± .15 | −31** | 0.82 ± .12 | +5.1 |
|  |  | 0.3 | 25.7 ± 7.8 | 1.09 ± .06 | −30*** | 0.52 ± .07 | −33* |
|  |  | 1.0 | 36.5 ± 7.9* | 0.90 ± .11 | −42*** | 0.35 ± .03 | −55*** |
|  |  | 3.0 | 49.8 ± 6.2*** | 0.99 ± .05 | −37*** | 0.27 ± .03 | −65*** |
| b | Control | — | −24.3 ± 19.9 | 1.87 ± .14 | — | 0.74 ± .40 | — |
|  | DCHA | 5.0 | 19.5 ± 5.8 | 1.30 ± .08 | −30** | 0.70 ± .05 | −5.4 |
|  |  | 10.0 | 33.3 ± 5.5* | 1.14 ± .04 | −39*** | 0.33 ± .06 | −55 |
|  |  | 25.0 | 30.3 ± 5.7* | 1.00 ± .05 | −47*** | 0.39 ± .04 | −47 |
|  | Phenylbutazone | 25.0 | 24.0 ± 6.3 | 1.04 ± .05 | −44*** | 0.45 ± .13 | −39 |

*p ≦ 0.05
**p ≦ 0.01
***p ≦ 0.001

The results show that DCHA is effective at doses from 3–300 mg/kg. (orally) using left paw edema (i.e. immunologically induced inflammation) as the major parameter. Using the right paw edema (i.e. the injected paw) at 4 days as a measure of acute, non-specific inflammation, DCHA is active at doses from 10–300 mg/kg. (orally). Rats receiving 100 and 300 mg/kg., which are doses 3-10 times the ceiling effect of DCHA, did not show any toxic signs or loss of body weight. In fact, significant weight gains of 51 and 58 g., respectively, were measured at these high doses. The estimated $ED_{50}$ of DCHA in this test is 15 mg/kg., while that of indomethacin is 0.9 mg/kg. and that of aspirin has been assessed at approximately 140 mg/kg. Thus, DCHA shows significant anti-inflammatory activity in the adjuvant arthritis test.

B. Periodic Administration

Adjuvant arthritis is induced as described in A. above, but drugs are administered only on days 2, 3, 4 or on days 8, 9, 10. The results are summarized in Table 4, which also shows results for a daily dosing regimen for comparison.

TABLE 4

| Treatment | Dosing Regimen | Oral Dose mg/kg | Change In Body Weight (mean ± S.E.) 0–16 days | Increase in Right Paw Volume (ml.) (mean ± S.E.) 0–4 days | % Change of Right Paw Edema at Day 4 | Increase in Left Paw Volume (ml.) (mean ± S.E.) 0–16 days | % Change of Left Paw Edema at Day 16 |
|---|---|---|---|---|---|---|---|
| Control | Daily (0–15)[a] | — | 11.9 ± 6.3 | 1.37 ± 0.07 | — | 0.74 ± 0.10 | — |
| DCHA | Daily (0–15)[a] | 2 | 8.9 ± 7.8 | 1.60 ± 0.08 | +17 | 0.82 ± 0.18 | +12 |
|  |  | 6 | 6.0 ± 4.8 | 1.03 ± 0.06 | −24 | 0.62 ± 0.04 | −16 |
|  |  | 18 | 18.3 ± 6.7 | 0.81 ± 0.07 | −41*** | 0.26 ± 0.05 | −65** |
| DCHA | Days 2,3,4 | 10 | 14.7 ± 11.7 | 0.92 ± 0.07 | −33** | 0.58 ± 0.13 | −22 |
| DCHA | Days 8,9,10 | 10 | 10.5 ± 7.9 | — | — | 0.31 ± 0.06 | −58* |

[a]Except weekends
*$p \leq 0.05$
**$p \leq 0.01$
***$p \leq 0.001$

In short term dosing regimens, DCHA is active in days 8, 9, 10 but less so in days 2, 3, 4.

EXAMPLE 8

The tests of Example 7 are repeated, but dosing with (5H-dibenzo[a,d]cyclohepten-5-ylidene)acetic acid (DCHA) and indomethacin is carried out only on days 16, 17 and 18, and ten rats are used in the test. The changes in left paw edema are measured at the end of 19 days, 23 days and 30 days. The results are summarized in Table 5.

TABLE 5

| Treatment | Oral dose mg/kg | Increase in left paw edema ml. (day 0–19) | % Change from Control | Increase in left paw edema ml. (day 0–23) | % Change from Control | Increase in left paw edema ml. (day 0–30) | % Change from Control |
|---|---|---|---|---|---|---|---|
| Control | — | 1.01 ± 0.09 | — | 0.96 ± 0.10 | — | 1.51 ± 0.13 | — |
| DCHA | 10 | 0.78 ± 0.11 | −20 | 0.82 ± 0.13 | −15 | 1.20 ± 0.16 | −21 |
|  | 30 | 0.75 ± 0.11 | −26 | 0.87 ± 0.16 | −10 | 1.07 ± 0.17 | −29 |
|  | 90 | 0.59 ± 0.06 | −42** | 0.73 ± 0.16 | −24* | 1.03 ± 0.11 | −32* |
| Indomethacin | 0.33 | 0.70 ± 0.11 | −31* | 1.02 ± 0.14 | +6 | 1.41 ± 0.20 | −6 |
|  | 1.00 | 0.62 ± 0.05 | −40** | 1.00 ± 0.06 | +4 | 1.18 ± 0.10 | −22 |
|  | 3.00 | 0.41 ± 0.06 | −60*** | deaths 6/10 | — | deaths 6/10 | — |

*$p \leq 0.05$
**$p \leq 0.01$
***$p \leq 0.001$

The results show that (5H-dibenzo[a,d]cyclohepten-5-ylidene)acetic acid provides a significant decrease in the left paw edema of rats with established adjuvant arthritis, and that unlike indomethacin, there is no significant return to pretreatment or even higher edema levels, even at the end of 30 days or 12 days after the last dosing. In fact, six out of ten rats had died by the 23rd day when dosed with 3.00 mg/kg. of indomethacin on days 16, 17 and 18.

EXAMPLE 9

Since prostaglandins are important in the regulation of mucosal blood flow in the stomach and small intestines, and since experimental evidence exists which shows that indomethacin has a marked inhibitory effect on prostaglandin synthesis in gastric mucosa, it is postulated that inhibition of prostaglandin synthetase activity may be a causative factor in gastric ulceration by non-steroidal anti-inflammatory drugs such as indomethacin and the salicylates.

Therefore the effect of (5H-dibenzo[a,d]cyclohepten-5-ylidene)acetic acid (DCHA) on the formation of $PGE_2$ from $^{14}$-C-arachidonic acid in the microsomal fraction of sheep vesicles is assayed by the following procedure.

Frozen sheep seminal vesicles are cleaned of fat and connective tissue and then minced. Ten grams of the minced tissue are homogenized in 20 ml. of 0.125 M Na-EDTA buffer, pH 8.3, employing polytron homogenizer. The homogenate is then centrifuged at 1,200×g. for 10 minutes and the resulting supernatant filtered through two layers of cheese cloth. The filtrate is then centrifuged at 10,000×g. for 20 minutes. The supernatant is then centrifuged at 105,000×g. for 1 hour. The precipitate is dissolved once with Na-EDTA buffer and recentrifuged at 105,000×g. for 1 hour. The final microsomal fraction is then dissolved in 1.0 ml. of Na-EDTA buffer and stored in a freezer.

The incubation buffer medium (1.0 ml. total) consists of 500 μg of lyophilized bovine serum albumin, $5 \times 10^{-4}$ M hydroquinone, $1.0 \times 10^{-2}$ M reduced glutathione, $3 \times 10^{-6}$ M $^{14}$C arachidonic acid (AA) in 0.02 ml. of methanol, 0.01 ml. of the tested drugs in methanol at the desired concentrations, and the microsomal fraction (1.2 mg. protein/ml. incubation medium). This medium is incubated for one hour at 37° C. At the end of this period, enzyme reaction is terminated by the addition of 0.25 ml. of 1 N HCl. 15 μg of non-radioactive Prostaglandin $E_2$ ($PGE_2$), Prostaglandin $F_{2\alpha}$($PGF_{2\alpha}$) and AA (5 μg each) in an ethanol solution is then added to all of the acidified reaction mixtures. The reaction products are extracted with ethylacetate (2×2 ml.) and the total organic solution of 4 ml. is washed with 1.0 ml. of triple distilled water. 3.0 ml. of the total ethylacetate solution is removed and evaporated to dryness under nitrogen gas. The residue is then re-dissolved in 50 μl. of 100% ethanol and spotted on silica gel GF plates and subjected to chromatograph. Only the organic phase of the ethyl acetate:water:iso-octane:acetic acid system (11:10:5:2) is used as solvent in the chromatography system.

After exposure to iodine vapor, the $PGE_2$ and AA spots are scraped from the TLC plate, put into separate vials, and mixed with 10.0 ml. of Instagel scintillation cocktail for counting in a Nuclear-Chicago Mark II liquid scintillation counter.

Results are expressed as counts per minute (cpm), evidencing in vitro $PGE_2$ biosynthesis.

The results are summarized in Table 6.

TABLE 6

| Treatment | Drug Concentration (μg/ml) | cpm (× 1000) |
|---|---|---|
| Control | — | 9.2 ± .6 |
| DCHA | 30 | 6.6 ± .3 |
|  | 50 | 5.2 ± .4 |
|  | 60 | 5.1 ± .2 |
|  | 100 | 3.0 ± .1 |
|  | 120 | 3.3 ± .4 |
|  | 150 | 2.1 ± .3 |
|  | 200 | 2.0 ± .1 |

From this, the 50% inhibitory concentration for DCHA is calculated to be 64.2 μg/ml., while indomethacin and aspirin have been shown to inhibit prostaglandin synthetase activity by 50% at 0.5 μg/ml. and 35 μg/ml., respectively. Thus, as compared to aspirin or indomethacin, DCHA does not have an appreciable inhibitory effect on prostaglandin synthetase activity.

EXAMPLE 10

(5H-Dibenzo[a,d]cyclohepten-5-yldene)acetic acid is tested for gastric irritation in the rat according to the following procedure.

Male Charles River rats (Sprague-Dawley) weighing between 140-160 gm. are deprived of food for 18 hr. with water ad lib. The rats are divided into groups 6-10 and dosed by the oral route with test compound, on a mg/kg. body weight basis, or vehicle control, 0.5% carboxymethylcellulose, in a volume of 3 ml. per rat. Four hours after dosing, the rats are decapitated and exsanguinated. Stomachs are removed and examined for gastric swelling and then opened and washed for visual inspection of gastric ulcers. Only one lesion or gastric bleeding is necessary for a positive response. Data is reported quantally.

The results of the tests for gastric secretion and gastric ulceration by (5H-dibenzo[a,d]cyclohepten-5-ylidene)acetic acid (DCHA), aspirin and indomethacin are summarized in Table 7.

TABLE 7

| Treatment | Oral dose mg/kg | Number of Animals With Gastric Ulcers | Gastric Swelling* |
|---|---|---|---|
| DCHA | 60 | 0/6 | 0/6 |
|  | 120 | 0/6 | 0/6 |
|  | 240 | 0/6 | 0/6 |
|  | 480 | 0/6 | 0/6 |
| Aspirin | 60 | 0/10 | 0/10 |
|  | 120 | 0/10 | 3/10 |
|  | 240 | 0/10 (blood present 3/10) | 6/10 |
|  | 480 | 0/10 (blood present 7/10) | 10/10 |
| Indomethacin | 2.5 | 0/9 | 0/10 |
|  | 5.0 | 9/10 | 0/10 |
|  | 10.0 | 10/10 | 0/10 |
| Control | — | 0/10 | 0/10 |

*Enlarged or distended stomachs containing fluid or digested material (increased gastric secretion).

The results show that (5H-dibenzo-[a,d]cyclohepten-5-ylidene)acetic acid has no effect on gastric secretion and evidences no gastric ulceration at doses up to 480 mg/kg., while both aspirin and indomethacin show significant effects on the gastric tract at dosage levels indicated for the treatment of inflammatory conditions.

The experimental test and assay results show (5H-dibenzo-[a,d]cyclohepten-5-ylidene)acetic acid to be a significant non-steroidal anti-inflammatory agent, several times more potent than aspirin in chronic inflammatory disease mediated mainly through immunological mechanisms, with no apparent toxicity at high doses, no appreciable activity in the inhibition of prostaglandin synthetase activity and neither causing gastric irritation nor affecting gastric secretions. The currently used non-steroidal anti-inflammatory drugs of choice, namely aspirin and indomethacin, not only have appreciable effects on prostaglandin synthetase activity but are also proven gastric ulcerogens, especially when used in long-term therapy of chronic inflammatory conditions.

What is claimed is:

1. A method of treating inflammation in a mammal which comprises administering thereto an effective amount of a compound having the formula:

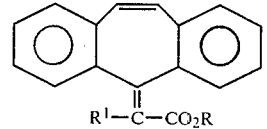

where R is hydrogen or an alkyl group of 1-4 carbon atoms, $R^1$ is hydrogen or an alkyl group of 1-4 carbon atoms, and pharmaceutically acceptable salt thereof.

2. The method of claim 1 wherein R and $R^1$ are both hydrogen.

3. The method of claim 1, wherein R is ethyl and $R^1$ is hydrogen.

4. The method of claim 1, wherein R is hydrogen and $R^1$ is methyl.